United States Patent [19]
Jalonen et al.

[11] Patent Number: 5,571,534
[45] Date of Patent: Nov. 5, 1996

[54] DRUG FORMULATIONS FOR PARENTERAL USE

[75] Inventors: Harry G. Jalonen; Terttu M. Heikkilä; Hannu U. Jalonen, all of Turku; Lauri V. M. Kangas, Raisio; Risto A. S. Lammintausta; Kauko O. A. Kurkela, both of Turku, all of Finland

[73] Assignee: Orion-yhtymä Oy, Espoo, Finland

[21] Appl. No.: 244,549

[22] PCT Filed: Dec. 10, 1992

[86] PCT No.: PCT/FI92/00339
§ 371 Date: Jul. 7, 1994
§ 102(e) Date: Jul. 7, 1994

[87] PCT Pub. No.: WO93/11757
PCT Pub. Date: Jun. 24, 1993

[30] Foreign Application Priority Data

Dec. 10, 1991 [GB] United Kingdom .................... 9126209

[51] Int. Cl.⁶ ...................................................... A61K 9/14
[52] U.S. Cl. .......................... 424/479; 424/488; 424/493; 424/499; 514/646
[58] Field of Search ............................................. 514/646

[56] References Cited

FOREIGN PATENT DOCUMENTS

| | | |
|---|---|---|
| 1246446 | 12/1988 | Canada . |
| 0355604 | 2/1990 | European Pat. Off. . |
| 0359981 | 7/1993 | European Pat. Off. . |
| 8205611 | 10/1982 | France . |
| 3331459 | 3/1984 | Germany . |
| WO90/02141 | 3/1990 | WIPO . |
| WO90/05106 | 6/1990 | WIPO . |
| WO91/17749 | 11/1991 | WIPO . |

OTHER PUBLICATIONS

CA116:15328 Shah et al, "Human Albumin binding of tamoxifen in the presence of a perfluorochemical erythrocyte substitute", *J. Pharm. Pharmocology* 43(11), pp. 790–793. 1991.

CA(114)88647, 1990. Abstract only.

CA(104)139720, 1985. Abstract only.

Chemical Abstracts, vol. 116, No. 16, 20 Apr. 1992, p. 442, Abstract No. 158718p, "Solubilization and Stabilization of Drugs Through Cyclodextrin Complexation", Thorsteinn Loftsson et al.

Acta Pharm. Nord. 3 (4)215–217 (1991), "Solubilization and Stabilization of Drugs Through Cyclodextrin Complexation", Thorsteinn Loftsson et al.

Journal of Chromatography, 414, No. 1 (1987), 192–196, Biomedical Applications, "Seperation of Tamoxifen Geometric Isomers and Metabolites by Bonded–Phase β–Cyclodexrin Chromatography", R. Douglas Armstrong et al.

FEBS Letters, vol. 274, No. 1,2, Nov. 1990, pp. 107–110, "Mechanism of Inhibition of Lipid Peroxidation by Tamoxifen and 4–hydroxytamoxifen Introduced into Liposomes", Helen Wiseman et al.

Journal of Clinical Oncology, vol. 7, No. 9, (Sep.), 1989, pp. 1359–1364, "Toremifene: Pharmacologic and Pharmacokinetic Basis of Reversing Multidrug Resistance", Michael W. DeGregorio et al.

Drug Development and Industrial Pharmacy, 17(11), 1503–1549 (1991), "Cyclodextrins in the Pharmaceutical Field", O. Bekers et al.

*Primary Examiner*—Marianne M. Cintins
*Assistant Examiner*—Keith MacMillan
*Attorney, Agent, or Firm*—Burns, Doane, Swecker & Mathis, L.L.P.

[57] ABSTRACT

This invention relates to parenteral preparations of antiestrogens such as toremifene, desmethyl toremifene, tamoxifen or desmethyltamoxifen. The preparations can be emulsions, liposomes or aqueous solutions of cyclodextrin-drug complexes. Particularly the invention relates to a parenteral drug formulation comprising a complex having a 2-hydroxypropyl cyclodextrin component and including an active drug substance selected from the group consisting of toremifene, desmethyl toremifene, tamoxifen and desmethyltamoxifen or a pharmaceutically acceptable non-toxic salt thereof, said complex being present either in an aqueous solution or emulsion or loaded into a liposome.

4 Claims, No Drawings

DRUG FORMULATIONS FOR PARENTERAL USE

This application is a 371 of PCT/FI92/00339, filed Dec. 10, 1992 and published as WO93/11757 Jun. 24, 1992.

DRUG FORMULATIONS FOR PARENTERAL USE

This invention relates to drug formulations of antiestrogens, particularly antiestrogens comprising a triphenyl-butene moiety, for use in parenteral administration. Toremifene, desmethyl toremifene, desmethyl tamoxifen and tamoxifen are all examples of substituted triphenyl-butenes useful in cancer therapy. Reference is made to U.S. Pat. No. 4,696,949, U.S. Pat. No. 4,990,538 and U.S. Pat. No. 4,356,516. They can all be described with the formula

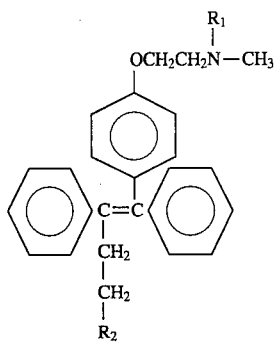

in which $R_1$ is $CH_3$ or H and $R_2$ is H or Cl.

The compounds mentioned above have the following values of $R_1$ and R2;

|  | $R_1$ | $R_2$ |
| --- | --- | --- |
| toremifene | $CH_3$ | Cl |
| desmethyl toremifene | H | Cl |
| tamoxifen | $CH_3$ | H |
| desmethyl tamoxifen | H | H |

A common feature of these antiestrogens is their poor solubility in water. Thus, parenteral administration of these drugs cannot be accomplished simply by an aqueous solution of the active ingredients.

There is a clear need for parenteral formulations of the anticancer antiestrogens. Injectable high-concentration toremifene formulations will have important clinical benefit 1) in the attempts to reach high concentrations in tissue. This is necessary especially when combinations of toremifene with cytotoxic drugs are given to a patient. As shown by DeGregorio et al (J Clinical Oncology, vol 7, No 9,1989: 1359–1364.) high plasma concentrations are more effective in reversing multidrug resistance than low concentrations. An injectable formulation enables high peak concentrations in blood and tissues without exposing the patient to long-term treatment;

2) when given locally into a tumor. This enables a high and efficacious concentration in the tumor to be achieved;

3) when used topically in a benign estrogen-dependent lesion like cystic mastalgia, where toremifene can be injected directly into a painful cyst;

4) when spreading toremifene topically onto palpable and subcutaneous breast cancer metastases;

5) when an intravesical installation is given for the therapy of superficial bladder cancer. In this indication toremifene may well be used together with other anticancer drugs to enhance their efficacy;

6) when an intraperitoneal solution is given for the treatment of certain types of overian cancer;

7) when other topical, estrogen-dependent lesions are treated with an antiestrogen.

The parenteral drug formulations according to this invention include emulsions, aqueous solutions of cyclodextrin—drug complexes and liposomes.

Dissolution properties of drugs can be significantly improved by complexation of the drug substance with cyclodextrins. Cyclodextrins (including α, β and Γ cyclodextrins and their derivatives) are all cyclic oligomers of glucose. The cyclodextrins can form inclusion complexes with drugs in that the drug molecule is included in the lipophile-seeking cavities of the cyclodextrin molecule. Therefore the cyclodextrins effectively solubilize lipophilic drugs into aqueous media. The use of cyclodextrins in the pharmaceutical field has been described e.g. in Drug Development and Industrial Pharmacy, 17(11), 1503–1549, 1991.

With respect to the antiestrogens mentioned above, however, no parenteral drug formulations based on complexation of the active drug substance with 2-hydroxypropyl cyclodextrins are known in the art. One object of this invention is a parenteral formulation based on a 2-hydroxypropyl cyclodextrin, preferably 2-hydroxypropyl β-cyclodextrin or 2-hydroxypropyl-Γ-cyclodextrin, complex including an active drug substance selected from the group consisting of toremifene, desmethyltoremifene, tamoxifen and desmethyltamoxifen or a pharmaceutically acceptable non-toxic salt thereof, said complex being present in an aqueous solution.

Emulsions of the antiestrogens mentioned above can be made by dispersing the drug or a cylodextrin complex of said drug into a pharmaceutically acceptable emulsifier, and optionally adding a stabilizing agent.

Parenteral administration of the drugs mentioned above may also be accomplished by aqueous solutions of liposomes containing said drug or a salt thereof. Liposomes are spherical particles in an aqueous medium, formed by a lipid bilayer enclosing an aqueous compartment. The lipid surface may be either unilamellar or multilamellar. The liposomes may be loaded with either hydrophobic or hydrophilic drug substances.

Another object of the invention is a parenteral formulation based on the drug substance as such loaded into liposomes. Such liposomes can be made by dissolving the drug or drug-cyclodextrin complex together with a phospholipid component, preferably DMPG (dimyristoylphosphatidylglycerol) and/or POPC (=1-palmitoyl-2-oleoyl-sn-glycero-3-phosphorylcholine), in a chloroform-methanol mixture, evaporating the solvent, dissolving the residue into water followed by homogenization. According to this invention liposomes can be made directly by dissolving the drug or the drug-cyclodextrin complex and phospholipid component directly in water without foregoing dissolving into chloroform-methanol mixture.

Another object of this invention is a parenteral formulation based on a 2-hydroxypropyl cyclodextrin, preferably 2-hydroxypropyl β-cyclodextrin or 2-hydroxypropyl Γ-cyclodextrin, complex including an active drug substance selected from the group consisting of toremifene, desmethyl toremifene, tamoxifen and desmethyltamoxifen or a pharmaceutically acceptable nontoxic salt thereof, said complex being loaded into a liposome.

Preparation of the Antiestrogen,-2-Hydroxypropyl Cyclodextrin Complexes

A weighed amount of 2-hydroxypropyl cyclodextrin was dissolved into distilled water by shaking with a shaker. The so formed clear solution was equilibrated with a large excess of antiestrogen at the boiling point. After removing the almost clear solution the excess of antiestrogen started to precipitate. The solution was kept overnight at room temperature and the excess of precipitated antiestrogen was removed by centrifugation.

Measurement by HPLC of the solubility of the antiestrogen in an aqueous solution of 2-hydroxypropyl cyclodextrin.

The fully automated HPLC apparatus (Hewlett-Packard, USA) consisted of a pump 1090, an autosampler and autoinjector (79847A) with an injection volume of 10 ul and a fixed wavelength UV detector, 280 nm (79881A). The chromatograms and peak areas were recorded with an integrator 3393. The separations were carried out at room temperature on a 35 * 4.6 mm stainless steel column (packed with 3-µm spherical octadecylsilanebonded silica particles; HS-3 C-18, (Perkin-Elmer, USA)

The mobile phase consisted of a mixture of acetonitrile: 0.05 M aqueous phosphate buffer containing 0.004 M of dimethyloctyl amine with a pH of 7.4. The flow rate was 0.8 ml/min.

Preparation of the Liposomes

1) Liposomes based on cyclodextrin-drug complexes and prepared by dissolving the components in an organic solution 2-hydroxypropyl-β-cyclodextrin (12 mg), POPC (32 mg), cholesterol (4 mg), DMPG (dimyristoylphosphatidylglycerol) (8 mg) and toremifene citrate (2 mg) were dissolved in choloroform-methanol (2:1) and evaporated. The residue was dissolved in water and homogenized by sonication (Labsonic U, 50 W). The stability of the solution was good; no turbidity was observed after one month in room temperature.

2) Liposomes based on cyclodextrin-drug complexes and prepared by dissolving and homogenizing components directly in water 2-hydroxypropyl-β-cyclodextrin (24 mg), DMPG (dimyristoylphosphatidylglycerol) (16 mg) and toremifene citrate (2 mg) were simultaneously dissolved in 2 ml water and homogenized by sonication (Labsonic U, 50 W). The final solution was as clear as the solution above. The mean particle diameter of these two solutions were about 100 nm (Nicomp 370/HPL high power laser option). The solution was stable after one week storage at room temperature.

3) Liposomes which were not based on cyclodextrin complexes

Preparation of these solutions was attempted by dissolving the components directly into water. The only composition which gave a clear or slightly opalescent solution was DMPG (16 or 32 mg), toremifene citrate (2 mg) dissolved and homogenized by sonication (50 W) in 2 ml water. The stability of the solutions were not however good enough; solutions became a bit turbid in one month storage at room temperature, e.g., the composition toremifene citrate (2 mg), DMPG (32 mg) and cholesterol (4 mg) was not able to dissolve and homogenized in 2 ml water.

These results indicate that stable liposomes cannot be achieved in the absence of a cyclodextrin component especially if the drug and phosphiolipid are mixed directly into water.

However, cyclodextrin-free liposomes can be made by mixing the ingredients first in chloroform/ethanol (2:1) as described above for the cyclodextrin-containing liposomes.

| Formulation | Solubility results |
|---|---|
| | Toremifene solubility mg of toremifene |
| | ml of cyclodextrin-water soln. |
| 500 mg β-HPC/ml of aqueous soln. | 87.7 |
| 250 mg β-HPC/ml of aqueous soln. | 53.0 |
| 125 mg β-HPC/ml of aqueous soln. | 21.7 |
| 63 mg β-HPC/ml of aqueous soln. | 14.1 |
| 25 mg β-HPC/ml of aqueous soln. | 7.4 |
| 0 mg β-HPC/ml of aqueous soln. | 0.3 |
| 500 mg Γ-HPC/ml of aqueous soln. | 125.4 |
| 250 mg Γ-HPC/ml of aqueous soln. | 61.1 |
| 125 mg Γ-HPC/ml of aqueous soln. | 36.3 |
| | Tamoxifen solubility mg of tamoxifen |
| | ml of cyclodextrin-water soln. |
| 500 mg β-HPC/ml of aqueous soln. | 67.4 |
| 250 mg β-HPC/ml of aqueous soln. | 43.3 |
| 125 mg β-HPC/ml of aqueous soln. | 23.5 |
| 63 mg β-HPC/ml of aqueous soln. | 13.3 |
| 25 mg β-HPC/ml of aqueous soln. | 6.1 |
| 0 mg β-HPC/ml of aqueous soln. | <1.0 |
| | Desmethyl toremifene solubility ml of desmethyl toremifene |
| | ml of cyclodextrin-water soln. |
| 125 mg β-HPC/ml of aqueous soln. | 21.0 |

β-HPC = 2-hydroxypropyl-β-cyclodextrin
Γ-HPC = 2-hydroxypropyl-Γ-cyclodextrin

The pharmacokinetics of the toremifene formulations described above, when give intravenously, resemble closely those of perorally given toremifene. However, during the first minutes and 1–2 hours the concentrations of the intravenously given drug are high, while the drug, when given per os, has not yet been absorbed completely from the gastrointestinal tract.

Preparation of Emulsions

Emulsions prepared by dissolving the drug in a commercial fat emulsion.

The commercial fat emulsion used was Emulsan®20% (manufacturer Leiras-Kabi Infusion Ltd., Finland). Different amounts of toremifene citrate were dissolved in Emulsan solution and homogenized by sonication (Labsonic U, 50 W). The toremifene concentrations were 10 mg/ml, 14 mg/ml and 20 mg/ml. After the homogenization the samples were filtered through the 0.2 µm, 0.45 µm and 1.2 µm filters.

The concentration of toremifene was determined from the filtrate with a spectrofotometric method using the wave length of 278 nm. The samples were dissolved in methanol and diluted in the concentration of 0.02 mg/ml.

The results are presented in the following table:

| Concentration before filtration [mg/ml] | Size of the filter [μm] | Concentration after filtration [mg/ml] |
|---|---|---|
| 10 | 0.2 | 4.4 |
|  | 0.45 | 4.0 |
|  | 1.2 | 4.4 |
| 14 | 0.45 | 4.3 |
|  | 1.2 | 3.7 |
| 20 | 0.45 | 3.6 |
|  | 1.2 | 3.6 |

The results show that the solubility of toremifene can be increased considerably by encapsulating the toremifene in an emulsion droplet.

We claim:

1. A parental drug formulation comprising an emulsion or liposome comprising a complex which comprises a 2-hydroxypropyl cyclodextrin component and an active drug component in which the active drug is selected from the group consisting of toremifene, desmethyl toremifene, tamoxifen and desmethyltamoxifen or a pharmaceutically acceptable non-toxic salt thereof.

2. A formulation according to claim 1 where the 2-hydroxypropyl cyclodextrin component is 2-hydroxypropyl-β-cyclodextrin.

3. A formulation according to claim 1 where the drug is toremifene or its non-toxic pharmaceutically acceptable salt.

4. A method of treatment of a mammal having an estrogen-dependent tumor comprising administering to said mammal an antitumor effective amount of a formulation according to claim 1.

* * * * *